United States Patent [19]

Crawford et al.

[11] Patent Number: 4,564,614
[45] Date of Patent: Jan. 14, 1986

[54] ANTIINFLAMMATORY METHODS

[75] Inventors: Thomas C. Crawford; Stanley L. Keely, both of Ledyard; David L. Larson, East Lyme; Joseph G. Lombardino, Niantic; James J. Maciejko, Mystic, all of Conn.

[73] Assignee: Pfizer Inc., New York, N.Y.

[21] Appl. No.: 695,518

[22] Filed: Jan. 28, 1985

Related U.S. Application Data

[63] Continuation-in-part of Ser. No. 659,602, Oct. 11, 1984, abandoned.

[51] Int. Cl.$^4$ .................. A61K 31/54; A61K 31/435
[52] U.S. Cl. ...................................... 514/222; 514/277
[58] Field of Search ................ 424/246; 514/222, 277

[56] References Cited
PUBLICATIONS

Dovgyallo et al., Klin, Med. (Mosk) 51, 57 (1973).
Litinskaya Vrech Delo. 1977, 93 (1977).
Rote Liste 1981: Abstracts 05–216 to 239, 265–284, 333–348, 407–459.
Schumacher et al., Am. J. Clin. Nutr. 28, 1200 (1975).
Lindenbaum et al., Nutr. Metabol. 17, 368 (1974).
Lemeshko et al., Sov. Med. 29, 33 (1966).
Gerold, Fortsch. Therapy 92 (Supplement), pp. 1–4 (1974).
Pietrogrande et al., Clin. Ter. 71, pp. 531–537 (1974).

*Primary Examiner*—Stanley J. Friedman
*Attorney, Agent, or Firm*—Charles J. Knuth; Albert E. Frost; Robert K. Blackwood

[57] ABSTRACT

An improved antiinflammatory composition and method of treating inflammation which employs a combination of a non-steroidal antiinflammatory agent such as piroxicam, or a pharmaceutically acceptable salt thereof, with pyridoxine.

3 Claims, No Drawings

ANTIINFLAMMATORY METHODS

CROSS REFERENCE TO RELATED APPLICATION

This application is a continuation-in-part of copending application Ser. No. 659,602, filed Oct. 11, 1984 abandoned.

BACKGROUND OF THE INVENTION

The present invention is concerned with an improved antiinflammatory composition and method of treating inflammation which employs non-steroidal antiinflammatory agent such as piroxicam, or a pharmaceutically acceptable salt thereof (particularly the ethanolamine salt of piroxicam) in combination with pyridoxine, a member of the vitamin $B_6$ complex. The generic names used here and elsewhere herein are from the USAN and the USP Dictionary of Drug Names, 1961-1981, Griffiths et al., ed., U.S. Pharmacopeial Convention Inc., Rockville, MD., 1984, have subsequently been assigned and published as official USAN names, and/or appear in The Merck Index 10th Edition.

Gastrointestinal irritation, including ulcers, is a side effect commonly associated, to one degree or another, with antiinflammatory agents. In many cases, individuals requiring such antiinflammatory treatment are precluded from enjoying the benefits thereof because of their susceptibility to such side effects. The present combination of a non-steroidal antiinflammatory agent with pyridoxine permits desirable antiinflammatory therapy while preventing or ameliorating said gastrointestinal irritation or ulcers.

There are no known reports bearing on the use of pyridoxine to reduce gastric side effects of non-stereoidal antiinflammatory agent. However, pyridoxine (1.1 mg/kg, injection) has been reported by Lindenbaum et al., *Nutr. Metabol.* 17, 368 (1974), to reduce the frequency of ulcers in the restrained mouse ulcer model. Pyridoxine by subcutaneous injection has been reported to alleviate the pain, but not promote the healing, of gastric ulcers [Lemeshko et al., *Sov. Med.* 29, 33 (1966)]; and in combination with anabolic hormones to produce a better antirelapse effect in patients with chronic gastritis, but not in patients with peptic ulcers [Dovgyallo et al., *Klin. Med.* (Mosk) 51, 57 (1973)]. Schumacher et al., *Am. J. Clin. Nutr.* 28, 1200 (1975) reported that patients with rheumatoid arthritis had lower than normal plasma levels of pyridoxal phosphate. Treatment of these patients with pyridoxine hydrochloride (50-150 mg/day) for 3 months resulted in increases (2-5 fold) in plasma levels of pyridoxal phosphate. However, no clinical improvements in the disease were noted. Even though most patients in this study were taking aspirin (and in many cases one or two additional agents) no comments were made on the side effect profile observed with this therapy (pyridoxine plus aspirin). In later studies it has been concluded that reduced levels of plasma levels of vitamin $B_6$ in patients suffering ulcer disease results from the antiulcer diet of the patient; although the duration of the disease was not dependent on $B_6$ levels, duration of exacerbation of the disease was dependent upon $B_6$ levels as one of several factors (Litinskaya, *Vrach. Delo.* 1977, 93).

Various combinations of vitamins $B_1$, $B_6$ and $B_{12}$, particularly in injectable form, have been indicated for use in various neuropathic disorders, such as neuritis and neuralgia (see the German "Rote Liste 1981", abstracts 05-439 to 05-447). Based on this rationale, clinicians have sought to influence nerve metabolism by the addition of these neurotropic vitamins to analgesic and/or antiinflammatory combinations in an effort to control the neuralgic symptoms frequently in rheumatic disease [for example, see Gerhold, Fortsch. Therapy, 92 (supplement), pp. 1-4 (1974) concerning a combination of phenylbutazone, ampyrone (aminophenazone), vitamins $B_1$, $B_6$ and $B_{12}$, and escin; see also Rote Liste 1981 abstracts 05-228 to 236, 05-267 to 284; 05-336; 05-407 to 430]. There is no prior evidence that such combinations improve the tolerance of antiinflammatory agents. Indeed in a typical, short-term clinical study with flufenamic acid in combination with vitamins $B_1$, $R_6$ and $B_{12}$, 5 of 26 patients were withdrawn from the study for lack of toleration [Pietrogrande et al., *Clin. Ter.* 71, pp. 531-537 (1974)].

SUMMARY OF THE INVENTION

The present invention concerns an improved antiinflammatory composition which comprises an antiinflammatory amount of a compound selected from the group consisting of aspirin, carprofen, diclofenac, diflunisal, etodolac, fenoprofen, fentiazac, flurbiprofen, ibuprofen, indomethacin, isoxicam, ketoprofen, meclofenamic acid, naproxen, niflumic acid, oxaprozin, piroxicam, pirprofen, sulindac, suprofen, tenoxicam and tolmetin; and the pharmaceutically acceptable salts thereof (particularly the ethanolamine salt of piroxicam), in combination with a gastric antiirritation and ulcer inhibiting amount of pyridoxine, or a pharmaceutically acceptable salt thereof.

The present invention is also concerned with an improved method for the treatment of inflammation in a mammal, including man, which comprises, in addition to treatment with an antiinflammatory amount of an antiinflammatory agent as listed above, treatment with a gastric antiirritation and ulcer inhibiting amount of pyridoxine or salt thereof.

DETAILED DESCRIPTION OF THE INVENTION

The antiinflammatory agents of the present invention are known. For example, The *Merck Index* 10th Ed., 1983 contains a monograph concerning piroxicam (no. 7378), as does the *Physicians' Desk Reference* (PDR), 38th Ed., pp. 1556-1557 (1984). The preferred ethanolamine salt of piroxicam is specifically disclosed in U.S. Pat. No. 4,434,164. The *Merck Index* 10th Ed. also contains monographs on aspirin (no. 863), carprofen (no. 1846), diclofenac sodium (no. 3066), diflunisal (no. 3127), etodolac (no. 3822), feoprofen (no. 3913), fentiazac (no. 3928), fluriprofen (no. 4101), ibuprofen (no. 4797), indomethacin (no. 4852), isoxicam (no. 5085), ketoprofen (no. 5142), melofenamic acid (no. 5600; the sodium salt is named meclofenamate sodium), naproxen (no. 6269), niflumic acid (no. 6377), oxaprozin (no. 6797), pirprofen (no. 7380), sulindac (no. 8863), suprofen (no. 8889), tenoxicam (no. 8980) and tolmetin (no. 9346). Pyridoxine is marketed as its hydrochloride salt as one of the vitamins of the $B_6$ complex (see The Merck Index 10th Ed., monograph no. 7882).

The clinical value of the present improved formulation in inhibiting gastric irritation and ulcers induced by antiinflammatory agents is reflected by appropriate animal studies. A typical experimental protocol, in which the ability of the test compound to prevent or reduce such induced gastric lesioning was determined, is found in the specific Examples below.

The present invention is readily carried out. The antiinflammatory agent or its salt is dosed in a mammal, particularly man, in its usual range, e.g., piroxicam is generally dosed in the range of 0.1 to 1 mg/kg/day, while indomethacin is generally dosed in the range 0.4–4 mg/kg/day with the usual frequency of dosage (generally a single daily dose in the case of piroxicam and a divided daily dose in the case of indomethacin). The vitamin $B_6$ agent, which can be dosed separately in single or multiple daily dosage, is generally dosed in the range of 0.06–40 mg/kg/day.

Preferably and conveniently, the antiinflammatory agent and gastric irritation and ulcer inhibiting agent of the present invention are co-administered in a single, combined formulation. This can be in a form suitable for parenteral administration, but is preferably in a form suitable for oral administration. The proportion of each drug in the combined dosage form will be in the ratio of the total daily dosage of each drug when dosed alone, in amounts suitable for single or divided daily doses as appropriate. The combined drugs will be dosed in single or divided doses. Single daily dosage will be most preferred in those cases where the in vivo half-life of the antiinflammatory agent is (like that of piroxicam) relatively long.

In the preferred oral route of dosage, the amount of piroxicam (or salt equivalent) for an average adult patient will generally be in the range of 5–50 mg/day in combination with 3 to 2000 mg/day of pyridoxine, an amount generally sufficient to inhibit gastrointestinal irritation or ulcers which could otherwise be induced by the antiinflammatory agent in patients susceptible to this side effect.

The combined compounds are administered alone or in further combination with pharmaceutically-acceptable carriers or diluents. For oral use, suitable pharmaceutical carriers include inert diluents or fillers, thereby forming dosage forms such as tablets, powders, capsules, and the like. These pharmaceutical compositions can, if desired, contain additional ingredients such as flavorings, binders, excipients and the like. For example, tablets containing various excipients, such as sodium citrate, are employed, together with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials therefor include lactose or milk sugar and high molecular weight polyethylene glycols.

The present invention is illustrated by the following examples. However, it should be understood that the invention is not limited to the specific details of these examples.

EXAMPLE 1

Protective Effect of Various Pyridoxine on Piroxicam-Induced Gastric Lesions in Rats Adult male "specific pathogen free" rats weighing 140–160 grams of the CD strain (Sprague-Dawley) were obtained from Charles River Breeding Laboratories (Kingston, N.Y.) The animals were acclimated for approximately one week and tested when they reached a body weight of 200–225 grams. The rats were fasted for 16 hours and randomized into groups consisting of 8 to 20 animals which were normalized with regard to their average body weight.

Gastric ulcers were induced in the animals by orally dosing them with a single 120 mg/kg dose of piroxicam (ethanolamine salt) in 2 ml. of aqueous 0.1% methylcellulose (pH=6.8). Those animals receiving a second medicinal agent separately received the second drug in an additional 2 ml. of the same medium at about the same time. Six and one-half hours later, the animals were sacrificed by cervical dislocation and autopsied. The stomachs were surgically removed, dissected along the greater curvature and rinsed with cold water. The stomachs were individually scored for both linear and punctuate lesions. The total number of lesions was used for scoring purposes. The data obtained from each group of rats was analyzed after calculation of the mean number ± the standard error of total gastric lesions. The values obtained were also compared to the controls which received only piroxicam by the two-tailed Student's T-Test for non-paired data. The protective effect of the second medicinal agent against piroxicam-induced ulcers is shown in Table I. These data show that pirbuterol, acetaminophen, fanetizole, doxepin and diazepam each significantly reduce piroxicam-induced gastric lesions in the healthy fasted rat.

TABLE I

Protective Effect of Various Forms of Pyridoxine Hydrochloride on Gastric Lesions Induced by the Ethanolamine Salt of Piroxicam

| Form of Vitamin $B_6$ | Oral Dose (mg/kg) | No. of Rats in Group | Lesions/Rat ($\overline{X}$ +/− SE)[b] | Significance $p < 0.05$[c] |
|---|---|---|---|---|
| (Control)[a] | 0 | 50 | 7.5 (1.2) | |
| | 3.3 | 10 | 7.0 (1.1) | − |
| Pyridoxine | 10 | 30 | 4.2 (1.2) | − |
| Hydro- | 33 | 50 | 3.9 (1.1) | + |
| chloride[a,d] | 100 | 20 | 2.7 (1.1) | + |

[a]All animals, including controls, received 120 mg/kg of the ethanolamine salt of piroxicam.
[b]Represents the mean value $\overline{X}$ +/− the standard error (SE).
[c]As determined by the Student's two tailed T-test for non-paired data.
[d]As calculated by linear regression analysis, an $ED_{50}$ (dose of pyridoxine hydrochloride required to inhibit 50% of control gastric lesion) of 33 mg/kg was determined.

EXAMPLE 2

Capsules—Piroxicam (20 mg) and Pyridoxine (1000 mg)

The following ingredients are combined in the following proportions by weight:

| | | |
|---|---|---|
| piroxicam (milled) | 20 | |
| pyridoxine hydrochloride (milled) | 1215 | (equivalent to 1000 as free base) |
| calcium carbonate | 350 | |
| polyethylene glycol, average molecular weight, 4000 | 515 | |

The mixture is thoroughly blended so as to obtain a uniform powder. Soft gelatin capsules containing 20 mg. of piroxicam and 1000 mg. of pyridoxine are prepared by filling suitably sized capsules with 2100 mg of the blend.

To make hard gelatin filled capsules, the amount of inert ingredients is adjusted so as to conveniently fill standard sized gelatin capsules containing the desired amount of each active component.

EXAMPLE 3

Tablets—Indomethacin (20 mg) and Pyridoxine (20 mg)

The following ingredients are combined in the following proportions by weight:

| | | |
|---|---|---|
| indomethacin (milled) | 20 | |
| pyridoxine hydrochloride (milled) | 24.3 | (equivalent to 20 of free base) |
| lactose | 183.7 | |
| hydroxypropyl methylcellulose | 3 | |
| sodium starch glycollate | 15 | |
| magnesium stearate | 4 | |

The mixture is thoroughly blended to form a uniform powder. Measured volumes of the powder, corresponding to 250 mg by weight, are compressed into tablets containing the desired potency of each active ingredient.

EXAMPLE 4

Tablets—Piroxicam (10 mg) and Pyridoxine (25 mg)

The following ingredients are combined in the following proportions by weight:

| | | |
|---|---|---|
| piroxicam ethanolamine salt (milled) | 23.68 | (equivalent to 20 of free base) |
| pyridoxine | 25 | |
| lactose | 226.32 | |
| hydroxypropyl methylcellulose | 4 | |
| sodium starch glycollate | 16 | |
| magnesium stearate | 5 | |

The mixture is thoroughly blended to form a uniform powder. The powder, in measured volumes corresponding to 300 mg. by weight, is compressed into tablets containing the desired potency of each active ingredient.

EXAMPLE 5

Capsules—Piroxicam (20 mg) and Pyridoxine (20 mg)

The following ingredients are combined in the following proportions by weight:

| | | |
|---|---|---|
| piroxicam | 20 | |
| pyridoxine hydrochloride | 24.3 | (equivalent to 20 as free base) |
| cornstarch | 652.7 | |
| magnesium stearate | 3 | |

The mixture is thoroughly blended so as to obtain a uniform powder. The resultant mix (700 mg fill weight) is filled into hard gelatin capsules of a suitable size so as to obtain capsules of the desired potency in each drug.

EXAMPLE 6

Tablets—Piroxicam (10 mg) and Pyridoxine (100 mg)

The following ingredients are combined in the following proportions by weight:

| | | |
|---|---|---|
| piroxicam | 10 | |
| pyridoxine hydrochloride | 121.5 | (equivalent to 100 as free base) |
| lactose | 244.5 | |
| hydroxypropyl methylcellulose | 4 | |
| sodium starch glycollate | 15 | |
| magnesium stearate | 5 | |

The mixture is blended to a uniform powder and compressed into tablets in measured volumes corresponding to 400 mg by weight to yield tablets of the desired potency in each drug.

What is claimed is:

1. A method for the treatment of inflammation in a mammal which comprises, in addition to treatment with an antiinflammatory amount of piroxicam or a pharmaceutically acceptable salt thereof, treatment with a gastric antiirritation and ulcer inhibiting amount of pyridoxine or a pharmaceutically acceptable salt thereof.

2. A method of claim 1 wherein the antiinflammatory compound is the ethanolamine salt of piroxicam.

3. A method of claim 1 wherein the antiinflammatory compound is piroxicam in its free acid form, and the pyridoxine is in the form of its hydrochloride salt.

* * * * *